(12) United States Patent
Ostermeyer et al.

(10) Patent No.: US 7,689,258 B1
(45) Date of Patent: Mar. 30, 2010

(54) DEVICE AND METHOD FOR DETERMINING OPTICAL CHARACTERISTICS OF BIOLOGICAL TISSUE

(75) Inventors: Martin Ostermeyer, Hannover (DE); Eckhard Ludwig, Hannover (DE); Stefan Zander, Celle (DE); Volker Bödecker, Hannover (DE); Holger Lubatschowski, Gehrden (DE)

(73) Assignee: Odicrain GmbH, Hannover (DE)

( * ) Notice: Subject to any disclaimer, the term of this patent is extended or adjusted under 35 U.S.C. 154(b) by 1724 days.

(21) Appl. No.: 10/130,231

(22) PCT Filed: Oct. 4, 2000
(Under 37 CFR 1.47)

(86) PCT No.: PCT/DE00/03486
§ 371 (c)(1),
(2), (4) Date: Oct. 8, 2003

(87) PCT Pub. No.: WO01/35815
PCT Pub. Date: May 25, 2001

(30) Foreign Application Priority Data
Nov. 17, 1999 (DE) .............................. 199 54 756

(51) Int. Cl.
*A61B 5/00* (2006.01)
(52) U.S. Cl. ........................... 600/310; 347/121
(58) Field of Classification Search ................ 600/309, 600/310, 336, 344, 473, 476; 374/121
See application file for complete search history.

(56) References Cited

U.S. PATENT DOCUMENTS

| | | | | |
|---|---|---|---|---|
| 4,222,389 A * | 9/1980 | Rubens | ........................ | 600/328 |
| 5,103,829 A * | 4/1992 | Suzuki et al. | ................ | 600/310 |
| 5,167,235 A * | 12/1992 | Seacord et al. | ............... | 600/474 |
| 5,340,215 A * | 8/1994 | Makita et al. | ................ | 374/121 |
| 5,381,796 A * | 1/1995 | Pompei | ....................... | 600/474 |
| 5,588,748 A * | 12/1996 | Nomura et al. | ............. | 374/158 |
| 5,638,162 A * | 6/1997 | Nettleton et al. | ........... | 356/4.02 |
| 5,653,238 A * | 8/1997 | Pompei | ....................... | 600/474 |
| 5,772,587 A * | 6/1998 | Gratton et al. | .............. | 600/310 |
| 5,908,384 A * | 6/1999 | West | ........................... | 600/310 |

(Continued)

FOREIGN PATENT DOCUMENTS

DE 19857148 A1 * 3/2000

(Continued)

*Primary Examiner*—Brian Casler
*Assistant Examiner*—Parikha S Mehta
(74) *Attorney, Agent, or Firm*—Novak Druce+Quigg; Gregory A. Nelson; Gregory M. Lefkowitz

(57) ABSTRACT

An appliance (1) for examining biological tissue comprises a light injection means (102) for injecting visible and/or close infrared light into the biological tissue, a detector (104) for converting light signals that exit the biological tissue into detection signals, an output device (130) allocated to the detector (104) for outputting information that depends on the detection signals and a shield (20; 106) allocated to the director (104) for shielding the detector (104) against extraneous light at least in the injected wave range. The appliance is also provided with a control device for controlling whether the arrangement of light injection means (102) and/or a detector and/or a shield (20; 106) is correct in relation to a substrate. The appliance can be used for examining biological tissue and supports the user for forcing the user to arrange the essential components of the examination device in the prescribed order before measuring.

12 Claims, 5 Drawing Sheets

U.S. PATENT DOCUMENTS

| | | | |
|---|---|---|---|
| 6,042,266 A * | 3/2000 | Cheslock et al. | 374/158 |
| 6,186,959 B1 * | 2/2001 | Canfield et al. | 600/559 |
| 6,195,574 B1 * | 2/2001 | Kumar et al. | 600/323 |
| 6,332,092 B1 * | 12/2001 | Deckert et al. | 600/476 |
| 6,453,183 B1 * | 9/2002 | Walker | 600/322 |
| 6,626,568 B2 * | 9/2003 | Sato et al. | 374/121 |
| 7,047,054 B2 * | 5/2006 | Benni | 600/323 |
| 2001/0053171 A1 * | 12/2001 | Sato et al. | 374/121 |

FOREIGN PATENT DOCUMENTS

JP          07286905 A   * 10/1995

* cited by examiner

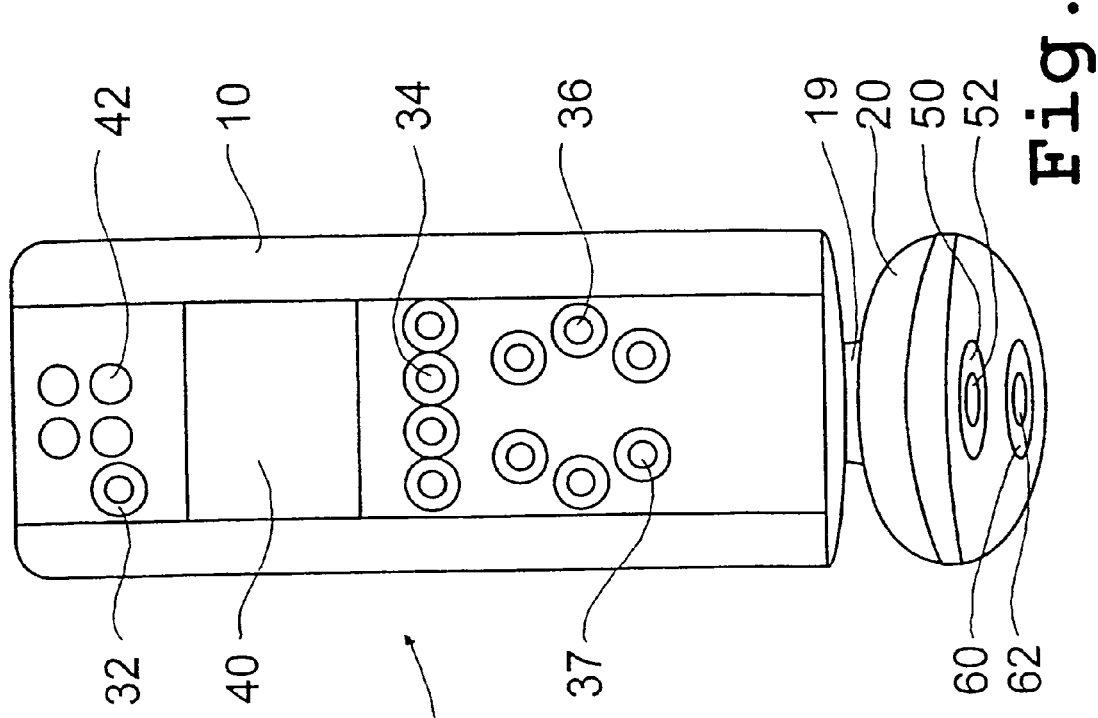
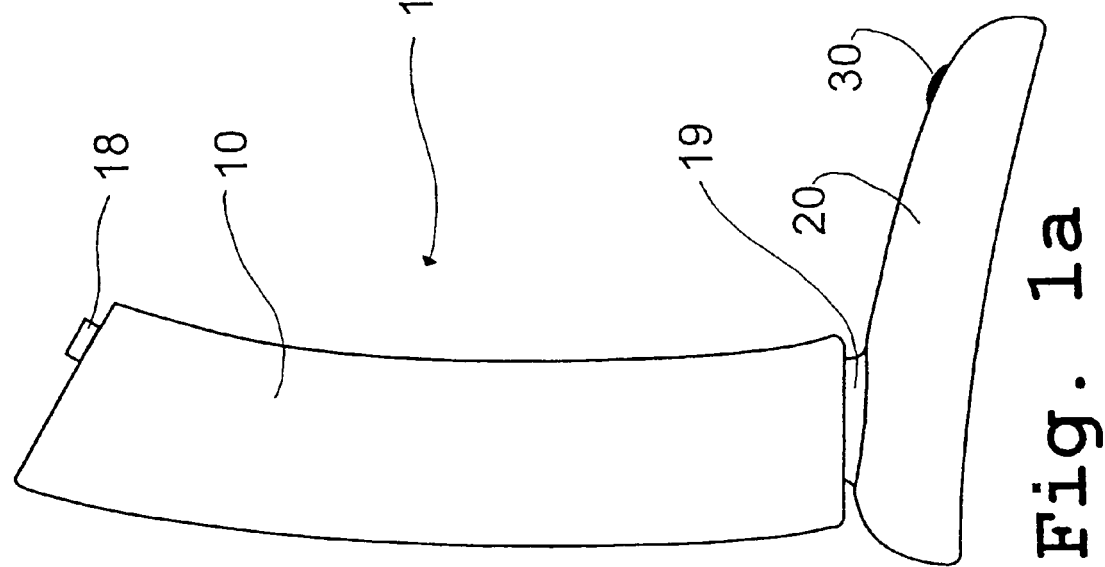

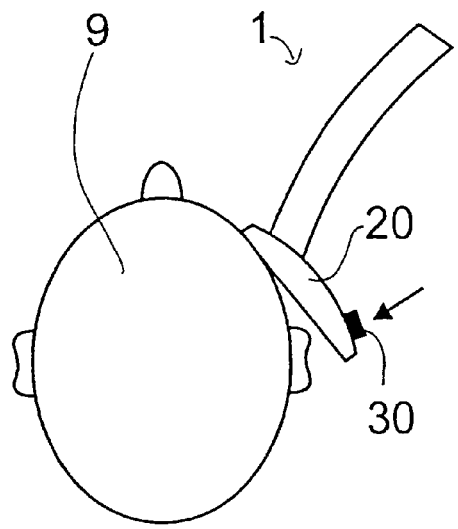
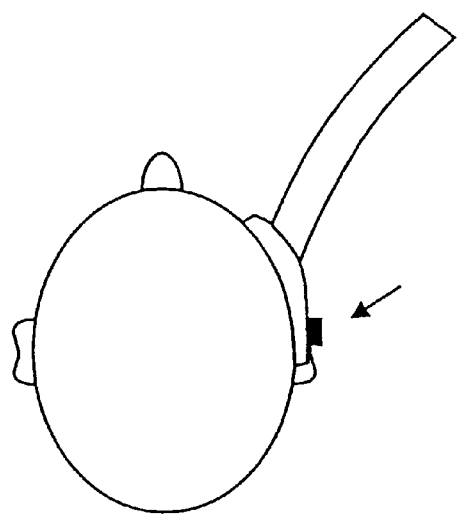
Fig. 3a                Fig. 3b
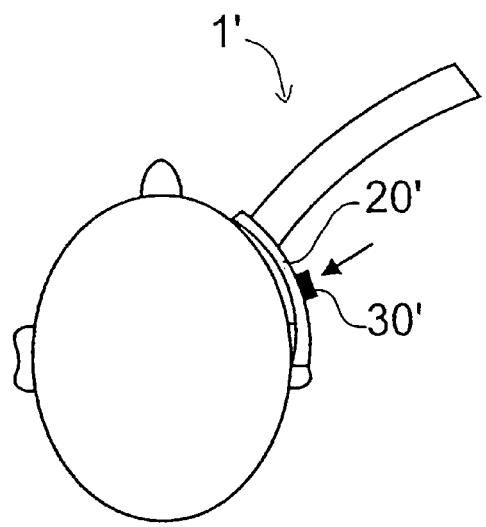
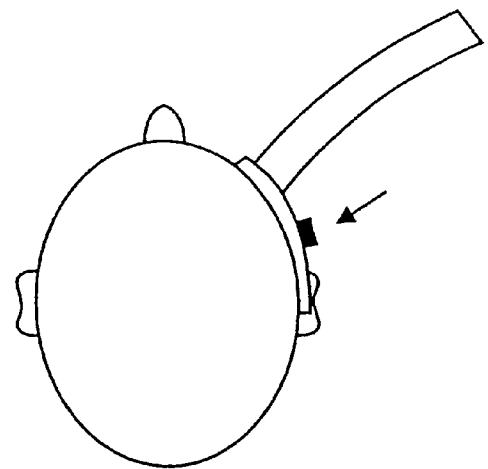
Fig. 3c                Fig. 3d

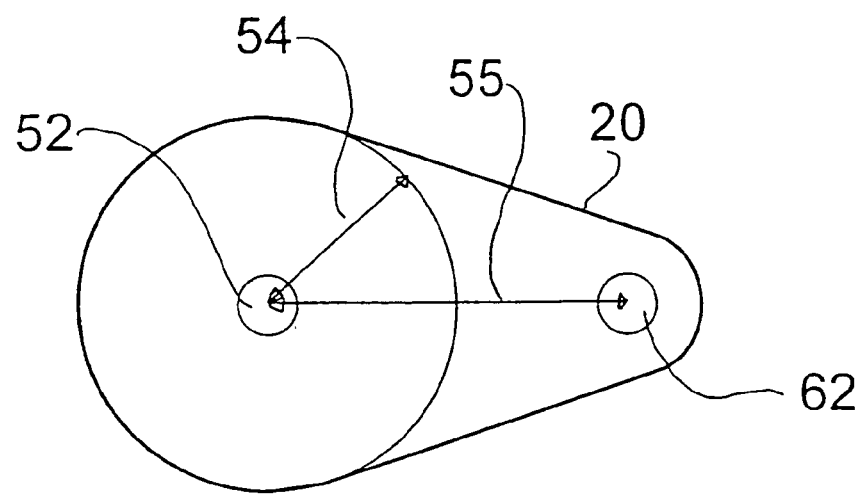
Fig. 4
Fig. 5
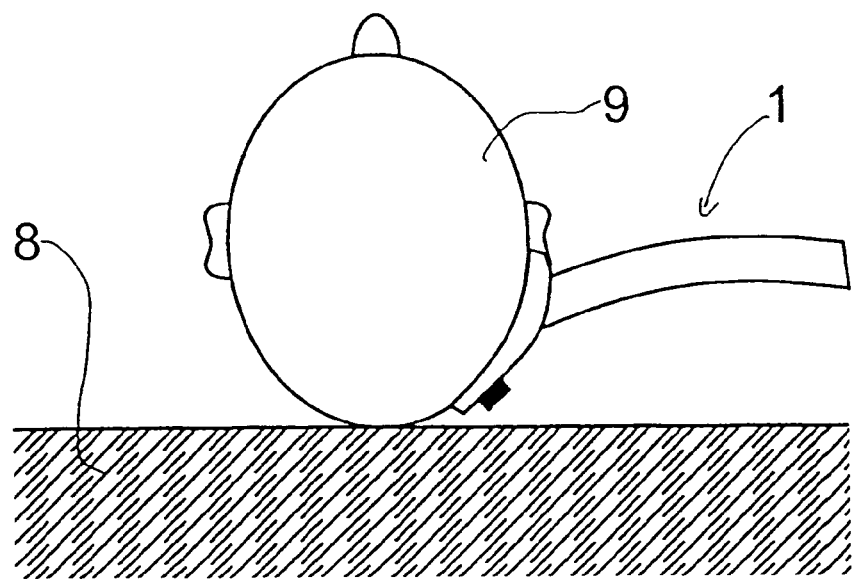

DEVICE AND METHOD FOR DETERMINING OPTICAL CHARACTERISTICS OF BIOLOGICAL TISSUE

CROSS REFERENCE TO RELATED APPLICATION

This application is a national stage of PCT/DE00/03486 filed Oct. 4, 2002 and based upon DE 199 54 756.4 filed Nov. 17, 1999 under the International Convention.

BACKGROUND OF THE INVENTION

1. Field of the Invention

The present invention concerns a device for examining biological tissue as well as a process in which the device is employed.

The device makes possible the determination of optical characteristics of biological tissue to be examined, and it includes:
- a light introduction means (for example a laser diode or the like) for introduction of visible and/or near-infrared light into the biological tissue,
- a detector for converting light signals emitted from the biological tissue into detection signals,
- a display or output device associated with the detector for output of information which depends upon the detection signals,
- a shield or barrier associated with the detector for shielding the detector against extraneous light at least in the introduced wavelength region.

For this, a few pointers:
- the light introduction means is in practice conventionally positioned at a prescribed position relative to a predetermined light entry location associated with biological tissue,
- the detector is in practice conventionally placed in a prescribed position relative to a predetermined light exit location associated with the biological tissue for detection of light following migration within the tissue and thereafter exiting the biological tissue,
- the output of the information resulting from the detection signal (measurement data) can occur in any of a number of ways, for example, per display, printer, loudspeaker or the like, and
- extraneous light is light which is not introduced by the light introduction means into the biological tissue to be examined.

2. Description of the Related Art

Devices of the above described type are already known and are in particular employed for examination of traumatic intracranial haematoma by means of NIR-spectroscopy (NIR=near-infrared), see Claudia S. Robertson et al, Journal of Biomedical Optics 2 (1), 31-41 (January 1997) as well as Shankar P. Gopinath et al, J. Neurosurg. 83:438-444, 1995.

SUMMARY OF THE INVENTION

The present invention also concerns in particular a device for determining the optical tissue characteristics of intracranial tissue, of which the measurement data can be consulted by a doctor as an aid for diagnosis following suspicion of the presence of bleeding in the brain, a stroke or the like.

In the above-mentioned research of Robertson et al as well as Gopinath et al, in each case an NIR-spectrometer of the type "RunMan" produced by the company NIM, Inc. of Philadelphia (Pa.), USA was employed. This device is an example of the type described in the introduction.

A number of devices of the above-described type are suitable for examining in non-invasive manner the optical characteristics of a particular target region of a biological tissue and in this way to provide information regarding metabolic characteristics, illnesses and other injuries. For the purposes of examination therein the light introduction means for introducing the visible and/or near-infrared light is placed upon an area of the region to be examined as selected by the user (light entry position), the detector is positioned a certain distance therefrom in a likewise position likewise selected by the user, and a shield is so arranged, that the detector in its detection position is shielded relative to the light entry position, at least substantially against extraneous light in the introduced wavelength region. Then, in the manner known in the art, visible or near-infrared light which has been introduced by the introduction means into the biological tissue and which again exits the biological tissue at the light exit position is detected by the detector as remaining or non-absorbed light. The detected data are finally evaluated in conventional manner (for example in an evaluation unit associated with the detector and conceivable as detector component) and subsequently displayed or printed by means of a downstream output device.

In the conventional devices and processes there frequently occurs the problem of measurements which cannot be interpreted. If for example, an unexpectedly strong light signal is detected by the detector during the measurement, then the user frequently doubts whether the light introduction means and the detector were positioned correctly relative to the biological tissue and whether the shield has performed its function. He would thus repeat the measurement one or more times, in order to increase his confidence.

It was thus the task of the present invention, to design a device of the described type in such a manner that the above-mentioned problem is at least minimized.

In accordance with the invention this task is solved thereby, that in a device of the above described type, a test device is provided for verifying whether a correct arrangement of light introduction means and/or detector and/or shield relative to a substrate has been provided.

This checking device is preferably so arranged, that in the case of an incorrect arrangement (a) it works together with the output device such that either an error signal or no information which is dependent upon the detection signal is output and/or (b) works together with the light introduction means such that the operation thereof is prevented and/or (c) works together with the detector such that the operation thereof is prevented.

Preferably the checking device includes for this one or more devices for determining, whether shielding and/or detector and/or light introduction means are in contact with a substrate (in practice this is frequently a biological tissue) in prescribed manner.

Preferred is a device of the above-described type, in which by means of the checking device
- the output device as well as in certain cases the light introduction means and/or the detector is activated (switched on) when the shield and/or the detector and/or the light introduction means is brought into contact with the substrate in prescribed manner and
- the output device as well as in certain cases the light introduction means and/or the detector are automatically inactivated (switched off) or remain inactive, when the shield and/or the detector and/or the light introduction means are not in contact with the substrate in prescribed manner.

And preferably the checking device is so arranged, that only upon simultaneous contact between (a) light introduction means and substrate as well as (b) detector and substrate the output device is activated (an output of the information dependent upon the detection signal can occur) and/or an operation of the light introduction means and/or an operation of the detector is permitted.

The inventive device assists the user, in that it forces him, prior to carrying out a measurement, to place or arrange the essential components of the examining equipment, namely shield, detector and light introduction means in a prescribed manner upon the biological tissue shielded from the environment such that an operation of the output device and/or the light introduction means and/or the detector is prevented, when the user has not correctly set up the arrangement (that is, in the prescribed manner), that is, in particular, no effective contact has been established between (a) shielding, detector and/or light introduction means and (b) substrate surface, then the user no longer experiences the irritation of a suspect measurement value. The user, after being prevented by the device from carrying out a measurement attempt, essentially undertakes an improved setting up (new contacting) of shield, detector and light introduction means relative to the biological tissue (substrate) which he desires to examine. If then in the case of a renewed attempt a measurement value is obtained, then the user can be substantially secure in the knowledge that he has established the prescribed examination conditions, at least insofar as it concerns the arrangement (contacting) of the mentioned equipment components, in the prescribed manner.

The inventive device therewith makes possible finally an accelerated optical examination of biological tissue. In the case of using the hitherto conventional devices, much time was wasted in examination due to avoidable or actual erroneous measurements.

The checking device can include a variety of different (checking) components.

For confirming a prescribed, correct arrangement (contacting) of the light introduction means and/or the detector the checking device can for example include a switch element associated with the light introduction means, wherein this switch element and light introduction means are so associated, that upon contact between the light introduction means and a substrate when the light introduction means and/or the shield is pressed against the substrate the associated switch element can be actuated, and/or the checking device includes a switch element for the detector, wherein this switch element and the detector are so associated, that upon contact between the detector and a positionally fixed substrate when the detector and/or the shield are pressed against the substrate the associated switch element can be actuated.

The respective switch element (or both switch elements) is then for example connected with a control unit, which activates the light introduction means and/or the detector and/or the output device, when the respective switch element (or both switch elements) are actuated.

If the inventive device includes a switch element for the light introduction means, wherein switch element and light introduction means are so arranged, that the switch element is activated by pressing the light introducing element and/or the shield against a substrate, and if the user employs this type of inventive device for examination of the brain, then he knows, that he must apply the light introduction means in the normal case by direct application to the head. He also knows that he would obtain particularly good measurements if he presses the light introduction means and the shield with a certain pressure against the scalp. The user would thus in each case undertake a general positioning of the light introduction means over the selected light introduction location. If a device in accordance with the invention, which is equipped as designed, the user is now forced to exercise a certain amount of pressure. For carrying out a measurement, for example on a convex head, the operator must actuate the switch element (for example a conventional switch), and for this a certain amount of force must be exerted upon the light introduction device at the light introduction means and/or the shield. The exercise of a force upon the light introduction means in the direction of light introduction brings about that the light introduction means is pressed more solidly than conventional against the scalp, and this ensures an optimal light introduction through the scalp and the scull into the brain. The exercising of a force upon the shield in the light introduction device accomplishes in analogous manner an improvement in the shielding of the detector against extraneous light.

Preferably the switch element can only be operated by exercising that amount of force upon the light introduction device which exceeds a predetermined minimal value. This minimal value corresponds to a minimal pressure of the light introduction means upon the light introduction location selected by the user.

As already mentioned, the checking device can, in place of or in addition to the switch element for the light introduction means, also include a switch element (switch) for the detector, wherein then this switch element and detector are so arranged, that upon operation of the switch element it is known that a force has been exercised upon the detector and/or the shield in the detection direction. The advantage of such a switch element-detector arrangement and its preferred design correspond to those of the above described switch element-light introduction means arrangement.

It is particularly advantageous, when the checking device includes a first switch element for the light introduction means as well as a second switch element for the detector, wherein the checking device can be designed to permit an output of the detection signals and/or an operation of the light introduction means and/or an operation of the detector preferably only upon simultaneous actuation of the first and the second switch elements.

In place of or in addition to the mentioned switch element-arrangement the checking device can also include a control element which is in communication with the detector, which compares the light signal received by the detector with a predetermined minimal or maximum threshold value and correspondingly carry out the above mentioned precautionary measures, for example, prevent an operation of the light introduction means and/or an output of the detection signals by means of the output device or, as the case may be, trigger a malfunction signal, when the light signal received by the detector exceeds a threshold value. With this design the detector can, independent of whether biological tissue is being examined at this time or not, measure the received light signal within a predetermined frequency range. Therein it is not distinguished, whether the received light originated from the light introduction means, or whether it in this case is extraneous light. If the detected light signal is too strong, then an external control unit downstream of the control element and the detector prevents the operation of the light introduction means and/or the output of information (measurement data) correlated with the detection signal. The received (too high) light signal value is preferably not even displayed to the user, instead, in the case of an erroneous measurement a preferably acoustic malfunction signal can occur (see above). In the case of correct positioning of the detector and detector-shield, for example upon the head of a subject or patient, the shield accomplishes its function and the light signal which may be measured by the detector may be extremely weak. In this case the light signal does not exceed a predetermined threshold, and the control unit thus permits the operation of the light introduction means and/or the output of measurement data.

Preferably in this case, with the presence of the control device, there is or are supplementally provided the above mentioned switch element-light introduction element-arrangement and/or switch element-detector-arrangement.

Additionally or alternatively to the mentioned checking components, the checking device can include, on the side of the shielding facing the biological tissue during operation of the device (for example, facing the head of a subject or patient) a device for monitoring or testing the contact of the shield and/or the light introduction device and/or the detector with the surface facing the biological tissue. This surface can for example be the scalp itself or a disinfection-effective protective foil provided on the scalp.

The control device can preferably include a measuring device for measuring the electrical resistance in a region between light introduction means and detector, wherein the checking device can be designed analogously to the above embodiments, that is for example such, that it prevents an output of the detection signal by means of the output device and/or the operation of light introduction means and/or the detector, when a predetermined resistance threshold is exceeded.

Alternatively or additionally the checking device can include a measuring device for measuring the electrical capacitance in the immediate environment of the light introduction means or the detector or in an area between light introduction means and detector, wherein the checking device can be designed analogous to the above embodiments, such that for example the operation of the light introduction means and/or the detector is prevented, when a predetermined capacitance threshold value is exceeded or not reached.

In particular in the field of the skin resistance and capacitance measurement the person of ordinary skill is familiar with measurement devices suitable for this purpose. These usually include electrical contact elements, which are to be pressed against the skin. If contact elements and skin do not make contact with each other correctly, then a too high of a resistance or as the case may be too high or too low of a capacitance value is measured.

It is advantageous, when the shield includes a soft, elastic deformable material for lying against a planar or curved substrate (foundation). In this manner a light-tight connection at the border between the substrate (for example, the surface of the biological tissue as substrate) and the light barrier can be achieved. In practice this mentioned planar or curved substrate usually concerns the outer surface of the head (particularly in the area of the scalp), however also the non-evasive examination of the brain of an embryo through a pregnant belly can for example be made possible thereby.

One substantial area of application for the inventive device will thus be for the examination of the (particularly human) brain. And for this application scenario the shielding is preferably so constructed, that it can be arranged relative to (a) the surface of the head near to the brain (the head outer surface in the area of the scalp) and (b) the detector, that the detector in its detection position is at least substantially shielded from extraneous light at least in the introduced wavelength region.

What is important is that the detector is shielded against extraneous light in the introduced and to be detected wavelength region. If the light introduction means introduces for example exclusively near-infrared light into the biological tissue, then the shield may be transparent for visible light. The user then has the possibility of viewing through the shield with the naked eye to check the correct placement of the detector on the light output location. The detector is in this case provided with a filter, which absorbs the visible light (which passes through the shield or barrier) and allows only the near-infrared light (which originates essentially from the light introduction means) to pass to the photosensor.

Preferably the shielding covers an area between the light introduction means and the detector, such that the detector and the there-between lying region can be brought into such an arrangement with the outer surface of a planar or curved substrate that the shielding not only precludes during operation of the light introduction means an erroneous signal of the measuring device due to introduction of extraneous light, but rather also prevents the propagation of light originating from the light introduction means along the substrate outer surface to the detector; it is included within the meaning of "propagation along the substrate outer surface" when the light originating from the light introduction means propagates along a segment within the tissue then passes along a segment outside of the tissue before reaching the detector.

Particularly preferred for examination of the brain is an arrangement wherein the light introduction means and the detector are spaced apart by a distance of 4 to 6 cm. This ensures a sufficient penetration of photons into the brain for an examination of superficial haematoma.

In particular in the area of emergency medicine the inventive device should be designed as a portable device. It should include a hand piece, which extends transverse or parallel to the shield surface of the shielding, that is, transverse or parallel to the surface of the shielding facing the biological tissue during operation.

In the portable or hand held device the grip piece includes preferably a housing for receiving an energy source and/or a display device and/or an evaluation unit and/or an input area. As energy source, conventional batteries (preferably rechargeable) can be provided.

In a preferred embodiment of an inventive device, which is designed to be particularly suitable as a hand held device for the emergency examination of a head, hand piece and light introduction means and/or hand piece and detector are connected to each other (a) rigidly or (b) flexibly relative to each other, via the pressure switch. Light introduction means and/or detector can be placed in their detection position by appropriate movement of the hand piece.

According to an alternative preferred embodiment of a hand held device for emergency examination of a head the shield includes an elastic area, in which the detector and the light introducing device are so embedded, that by the elastic deformation of the shield in the area lying between them a relative movement is carried out and their configuration can be conformed to various head shapes and/or curvatures. In such a design a spacer is preferably provided, which maintains substantially constant the distance between the detector and the light introduction means, measured along the—in certain cases, curved—shielding surface even with variation of the curvature of the shield surface. The spacer thus ensures to a limited extent that the bending zero line of the elastic shield is moved or displaced in the shield surface, and changes in distance between detector and light introduction means due to varying compression or stretching of the elastic region of the shield can be avoided.

If the shielding includes an elastic region between the detector and light introduction means, then it would typically also include a shield surface which, in the inoperative condition of the device, be essentially planar or curved, which on the basis of the elastic deformability of the shield can be brought into conformance with variously curved substrate surfaces (head surfaces).

BRIEF DESCRIPTION OF THE DRAWINGS

In the following the preferred embodiments of the inventive device will be described in greater detail on the basis of the figures. There is shown:

FIG. 1 a,b a side view of a front view of a inventive device;

FIG. 3 a-d schematic representation of the use of an inventive device;

FIG. 4 a schematic representation of the shield surface of an inventive device according FIG. 1 a,b; and FIG. 5 a schematic representation of a particular use of the device according to FIG. 1a.

DETAILED DESCRIPTION OF THE INVENTION

Figure 2:
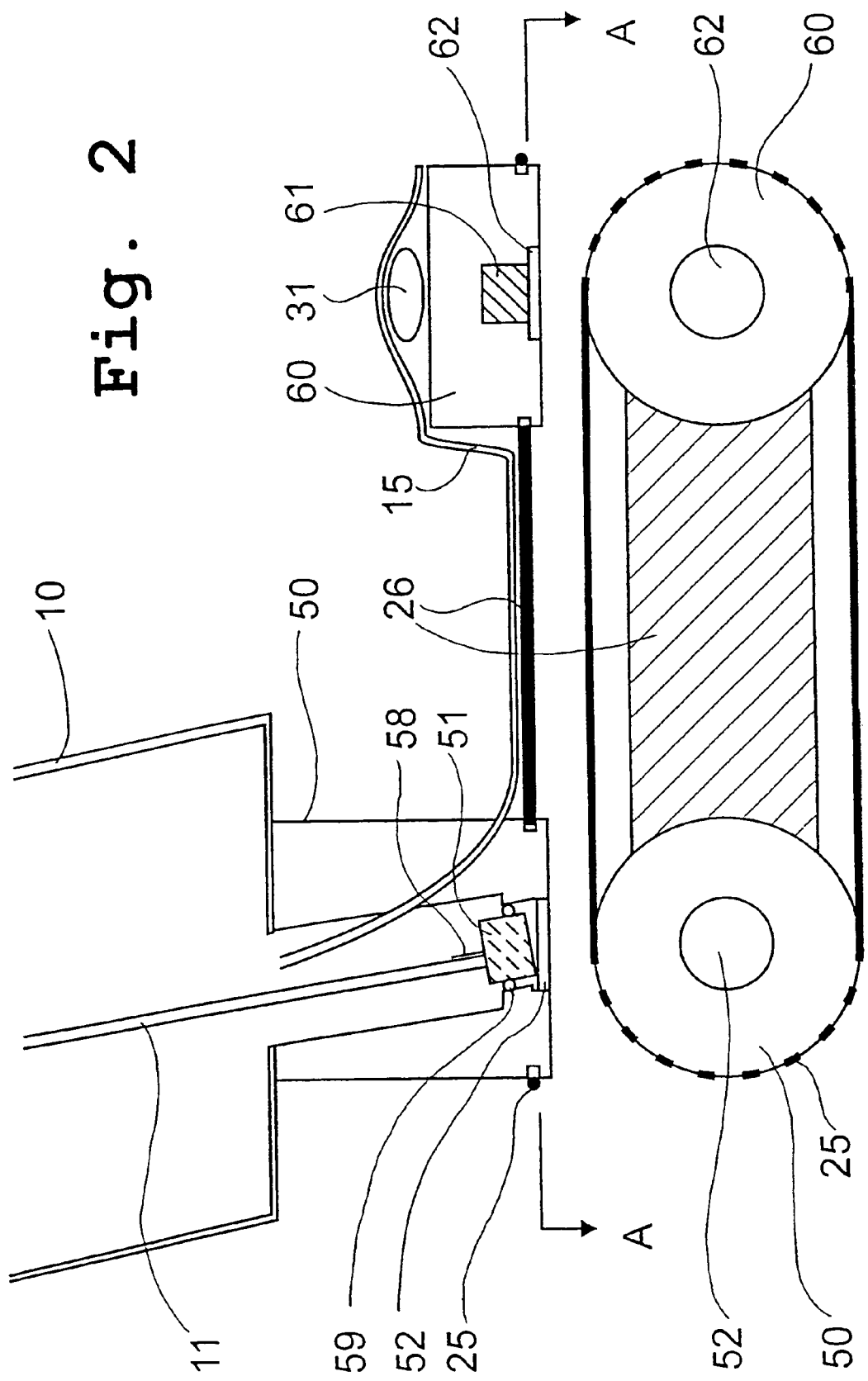
FIG. 2 a schematic cross-sectional view of the foot or base area of a device according to FIG. 1 a,b.

In FIG. 1 a,b a side and a front view of an inventive device is shown, which is suited in particular for detection of intracranial haematoma.

The device 1 includes a grip part 10, which is rigidly connected with a shield 20 via a connecting piece 19. The connecting piece 19 ensures that the shield 20 cannot as a whole (a) be rotated transverse to the grip piece 10 and (b) be displaced relative to the grip piece 10.

The grip piece 10 is approximately rectangular, wherein the "rectangle" however overall is curved on one side. Thereby the grip piece 10 includes a convex side, with two essentially parallel, planar casing surfaces on the sides thereof, while the remaining fourth casing surface runs complimentary to the convex side, that is, is curved concave.

The grip piece 10 is provided with an adapter 18, via which a storage battery (not shown) situated inside the grip piece 10, or another rechargeable energy source, can be recharged.

On the convex curved side of the grip piece 10 there are control elements, mainly an on/off switch 32, control switches as well as measuring point input keys or buttons 36, 37. With these measuring point keys 36, 37 the user of the device can in simple manner input at which head or scalp hemisphere and at which location (for example temporal, parietal, occipital) on this scull hemisphere a measurement is to be undertaken. All control elements 32, 34, 36, 37 are in the form of membrane or thin-film switches. They can thus be easily cleaned and are water-tight; this is particular of advantage for employment in emergency medicine.

All the sides of the grip part 10 are essentially flat, which increases the comfort level.

The grip part 10 further includes various information output means as a part of the output device.

The first output means is a display means 40 with a LCD-display, which if required could be back-lighted. In this manner a variety of information can be easily displayed to the user. By the backlighting it becomes possible to read the information even under less than ideal lighting conditions.

As further output means a loudspeaker (not shown) may be provided behind the operating pad membrane with acoustic output openings 42. Through these openings 42 the audio signal produced by the loudspeaker can be emitted in the opening direction well out of the housing of the grip part 10.

Embedded in the shielding 20 is (a) a light detector with housing 60 and window 62 as well as (b) a light introduction means with housing 50 and window 52. In the inside of the housing 50 and 60 there are provided photosensors or as the case may be light sources (here not shown, see however FIG. 2). The housing 50, 60 as well as the two windows 52, 62 respectively exhibit an essentially circular base surface (in FIG. 1b shown broken in perspective view). The housings 50, 60 are made of a solid, stiff material (aluminum, steel, hard plastic or the like). They thus prevent a displacement of the window 52, 62 relative to the components situated in the housing such as light source or photosensor (respectively not shown).

The shielding 20 has an approximately banana-like shape in a side view according to FIG. 1a. In the front view according to FIG. 1b it is to be recognized, that the shield surface is therein essentially ellipse or egg-shaped (see also FIG. 4). The shielding 20 is made of a flexible, soft material, adapted to completely absorb the light emitted in the wavelength region from the light introduction means. The shielding can be transparent for light of other wavelengths. Typically the shielding is made of black silicone, soft rubber, another elastic plastic or rubber.

The shielding 20 includes according to FIG. 1a a recess 30 for receiving a pressure switch (not separately shown in FIG. 1a), see however FIG. 2 in conjunction with the associated text of the description.

The cross-sectional views according to FIG. 2 show in detail the foot or base area of the grip piece 10 as well as the components essentially embedded in the shielding of the device introduced in FIGS. 1a and 1b. Therein for the purposes of overview the elastic shielding itself is not included.

In the upper image the grip part of the housing 10 facing the detector is shown in cross-section. On the lower edge thereof the detector attaches or connects with the housing 50.

The measurement window 52 provided on the bottom side of the housing is transparent for the measurement light emitted by the light emitting means (described below in detail), an essentially flat glass disk. In place of glass an appropriate transparent plastic material could just as well be used. The measurement window 52 is so embedded in the housing 50 and so sealed with its edges with respect to the housing 50 (adhered or the like), that in operation no body fluids or sweat can penetrate into the housing.

Behind the measurement window 52 there is provided a photosensor-component 51. This will be an electronic photosensor, which depending upon the strength of the light signal meeting it produces a specific measurement signal. The photosensor component 51 is connected with the housing 50 via a circumscribing ring 59. Preferably the ring 59 is elastic, so that for example in the case of manufacturing variations, small movements of the photosensor component 51 relative to the housing 50 is made possible.

The photosensor component 51 is connected with a plate 11 via a connecting element 58, which extends in the inside of the grip part 10 and is adapted to the essential elements of the control electronics of the device. It is particularly advantageous, when via the connecting element 58 the necessary electronic connections to the plate 11 are produced also for the operation of the detector component 51. The person of ordinary skill is aware of a series of connecting possibilities which are available, in particular, a conventional plug-in connection can be employed.

The photosensor component 51 or the detector housing 50 can, departing from the representation according to FIG. 2, be connected via a pressure switch (pressure-switch element) with the plate 11 or the grip part 10, which is operated by the relative movement of the detector-component 51 (or as the case may be detector housing 50) to the plate or grip part 50, as occurs for example during pressing of the detector against a positionally-fixed substrate. The operation of the pressure switch can be used as a precondition for the carrying out of a measurement, for example, in that the corresponding associated electrical connection means is supplied with an appropriate signal for operation of the switch at a check device on the plate 11, which prevents an operation of the output device (all or individual information-output means) and/or the light introduction means and/or the detector, when the switch is not actuated. Preferably the pressure switch does not allow itself to be actuated unless a force exercised upon it exceeds a minimal threshold value. This minimal threshold value corresponds to a minimal pressure of the detector against the user selected substrate.

In the end of the shield 20 which is moveable relative to the housing 50, the housing 60 is provided with a window 62 for light entry. The window 62 is comprised essentially of a transparent material, similar to the window 52. It can be secured to the associated housing 60 the same as the securing of the window 52.

Behind the window 62 is the actual light source 61 of the light emitting means. This could be a miniature laser, which emits a modulated (for example pulsed) light in the near-infrared wavelength range (600-900 μm). In place of a laser other light sources 61 could likewise be used, for example a diode or incandescent lamp. If the light source 61 emits in a wavelength range too broad for the examination purposes, it is necessary to provide a filter element at the light source 61 or prior to the photosensor component 51, which allows light of suitable wavelength for the examination being carried out to pass. Preferably at least one of the windows 52, 62 is a frequency filter (band pass filter).

On the essentially planar side of the housing 60 opposite to the window 62, there is provided a lens-shaped pressure switch 31. This pressure switch 31 is provided in the recess 30 (see FIG. 1*a*). The recess 60 can also be omitted, since it only serves the purpose of showing the user the position of the pressure switch 31. In place of the recess or protrusion 30, likewise other markings, such as for example color or a particular surface texture in a limited area on the shield 20 can be used.

The pressure switch 31 is connected with the checking device (that is the control circuit) via a connection 15 on the plate 11. The connection 15 is in the form of cables or in the form of a flexible strip (printed circuit). It extends from the housing 60 of the light source 61 through the housing 50 of the detector into the inside of the grip part 10 and to the checking device on the plate 11 (not shown). The function and operation of the switch is described in greater detail below on the basis of FIGS. 3*a* and 3*b*.

The housings 50, 60 are provided in their circumference surfaces respectively with recesses for a circumscribing band 25 as well as a spacer 26. The spacer 26 is comprised of a flat plate of a flexible elastic however essentially non-compressible sheet metal or plastic, of which the ends are adapted to the circular shaped circumference surfaces of the housing 50, 60. The band 25 is a stretch resistant nylon band, which is secured rigidly to the housing 50 and 60, in order to press these with the respective recesses against the spacer 26. By this arrangement it is in general prevented, that the light source 61 (against the elastic spring effect of the material of the shield 20) is moved away during a pulling or pressure loading in the plane of the spacer 26 or that the band 25 acting on the detector component 51 is pulled towards or from this. Besides this, the spacer 26 in combination with the band 25 contributes thereto, that the distance between detector 51 and light source 61, measured along the (in certain cases curved) shield surface (that is in approximately along the line detector window 52, detector-housing 50, spacer 26, light source housing 60, light source window 62) here means essentially constant, even when the light introduction means is displaced perpendicular to the plane of the spacer 26. This has the advantage, that due to the strong light absorption of biological tissue, particularly in examination of the human head, even small changes in space between light source and detector can result in strong differences in the intensity of the detectable light and therewith can introduce errors into the measured signal.

In the lower part of FIG. 2 a cross-sectional view in the direction of arrow A-A' is shown. Shown here is the housing 50, from the detector and light introduction means, as well as the respective centrally positioned window 52, 62 for the photosensor component or as the case may be the light source. Between the housing 50, 60 there is the spacer 26 (shown with cross-hatching in the figure). The band 25, shown with thick line, surrounds tightly the housing 50, 60; it is shown in dashed lines where it engages in the appropriate recess of the respective housing 50, 60.

The person of ordinary skill recognizes, that the use of the band 25 can be dispensed with, when the spacer 26 is so designed, that it at least partially surrounds the housings 50, 60 or is tension resistant connected with the housings and thus prevents that the housings 50, 60 can be moved apart from each other in the plane of the spacer 26.

In FIG. 3*a-b* the use of the inventive device 1 from FIGS. 1*a-b* and 2, and in FIG. 3*c-d* the use of an inventive device 1' with slightly modified shielding, is shown. A repetition of the reference numbers in FIGS. 3*b-d* for identical components was dispensed with.

It is shown in FIG. 3*a*, how the brain bleeding detection device 1 (shown schematically) is applied to the temporal area of the head 9. The user holds the device 1 in his hand. The operating element (see operating elements 36, 37 in FIG. 1*b*) are within reach of the thumb, whereby a rapid manipulation of the device 1 is facilitated.

As preparation for taking the measurement the user applies the device 1 first with the shield 20 in the area of the detector-housing 50 upon the surface of the head 9. If the device 1 includes a pressure switch at the detector, then this is actuated upon sufficient application pressure.

During this application of the device 1 the light source sided end of the shield 20 remains free. With the free finger of the leading hand (or with the second hand) the user presses upon the protrusion 30 and in the direction of the surface of the tissue to be examined (in the direction of the arrow). Thereby this side is deflected out of its rest position and pressed to make contact with the head surface (see FIG. 3*b*). As soon as the elastic shielding 20 lies tightly against the skin head, that is, within the projection 30 (and below the there below situated pressure switch), the head 9 exercises effective pressure upon the switch via the housing of the light producing means via the projection 30. The pressure switch is only then actuated, when a (pressure) force is exercised upon it, which exceeds a certain minimum value. This minimal value corresponds to a device specific minimum pressure value of the light introduction means on the location selected by the user (light introduction location). The checking device on the plate in the inside of the grip piece confirms that an operation of the light introduction means (or light source) is not possible without operation of the switch and provides to the output device a malfunction signal.

It is thereby insured, that the shielding 20 is brought into reliable contact with the head surface during measurement over essentially its entire shield surface. If this were not insured, then for example light could pass from the light source through a gap between head surface and shield 20 to the detector and cause an erroneous measurement signal; in the worst case this could even result in the detection of extraneous light by the detector. Thereby measurements would be substantially compromised or even be made impossible.

The person of ordinary skill recognizes, that in place of or in addition to a pressure switch below the projection or recess 30 also other check components could be employed, in order to insure, that the light introduction means (and the surrounding shielding) and the detector are correctly positioned during a measurement. In particular, using a conventional resistance measuring device the resistance between the light introduction means and the detector-housing can be measured and thereby the correct application of the light introduction means and detector housing on the biological tissue be verified. In similar manner the capacitance can be measured, wherein the checking device would allow the activation of the operative device and/or the light introduction means and/or the detector, and therewith allow a measurement of the biological tissue (in the illustrated example the head) only upon falling below or exceeding a predetermined appropriate threshold value.

Finally the checking device can also be designed to compare the light amount measured at the detector with a threshold value and to admit a measurement only then, when this threshold value is not exceeded. The threshold value is thereby so selected, that a measurement is prevented in the case of an unacceptably strong exposure to extraneous light.

If the checking device forbids the carrying out of a measurement (for example in the case of insufficient application pressure of the detector against the surface of the tissue to be examined), this can be indicated by the output device by an acoustic signal. Likewise the beginning and the end of the measurement process can be indicated with an acoustic signal. Finally a tone signal corresponding to the measured light intensity can be produced, such that the user can be informed regarding the light intensity without having to read the precisely quantified value from the display field.

In FIG. 3c-d a modified shielding 20' is shown. This is curved more strongly than the previously described shield. In order to produce a good seat of the shield 20' upon the surface, the user need not press on the light source end of the shield, but rather on a point between the grip piece 10 and the light introduction means housing. Typically the pressure switch is provided at this point; in FIGS. 3c and 3d this can be recognized by the position of the recess or projection 30'.

Similarly to the manner in which in FIG. 3b shows the shielding of the device of FIGS. 1a-b and 2, the pressure upon the projection 30' according to FIG. 3d brings about a complete pressing of the first strongly bowed shield 20' with its essentially total shield surface against the outer surface of a head 9. By this arrangement of the pressure switch 30' advantages are achieved as described above in FIG. 3b. Also the other manners of operating the checking device, as described above, can easily be achieved with the device according to FIG. 3c.

In FIG. 4 the shield surface of the shield 20 from FIGS. 1a-b, 2 and 3a-b is schematically shown. Shown are the windows 52 and 62 of the detector or as the case may be light introduction means. About the detector-window 52 an auxiliary circle with radius 54 is shown. Within this circle, of which the radius 54 is typically 3-6 cm, it is the primary task of the shield 20, to prevent a penetration of extraneous light, since otherwise the measured signal would be too strongly falsified. The area of the shield surface lying outside the auxiliary circle essentially serves to prevent the penetration of lateral light, that is, the penetration of measurement light originating from the light introduction device, which does not travel the entire way from the light introduction site to the detector light exit site within the head.

The two windows 52, 62 lie spaced apart from each other with a distance 55. The greater this distance 55, the deeper is the central penetration depth of the light emitted by the light emitter into the biological tissue to be examined and detected by the detector. For the detection of brain bleeding a spacing 55 of 3-7 cm has been found to be desirable, in particular a spacing 55 of 6 cm has been found to be particularly advantageous in relation to the amount of light to be introduced and the diagnostic reliability.

It is shown in FIG. 5 that with the inventive device according to FIG. 1a it is possible to examine in the parietal-occipital skull area, even if the head of the patient is resting upon a substrate 8.

Figure 6:
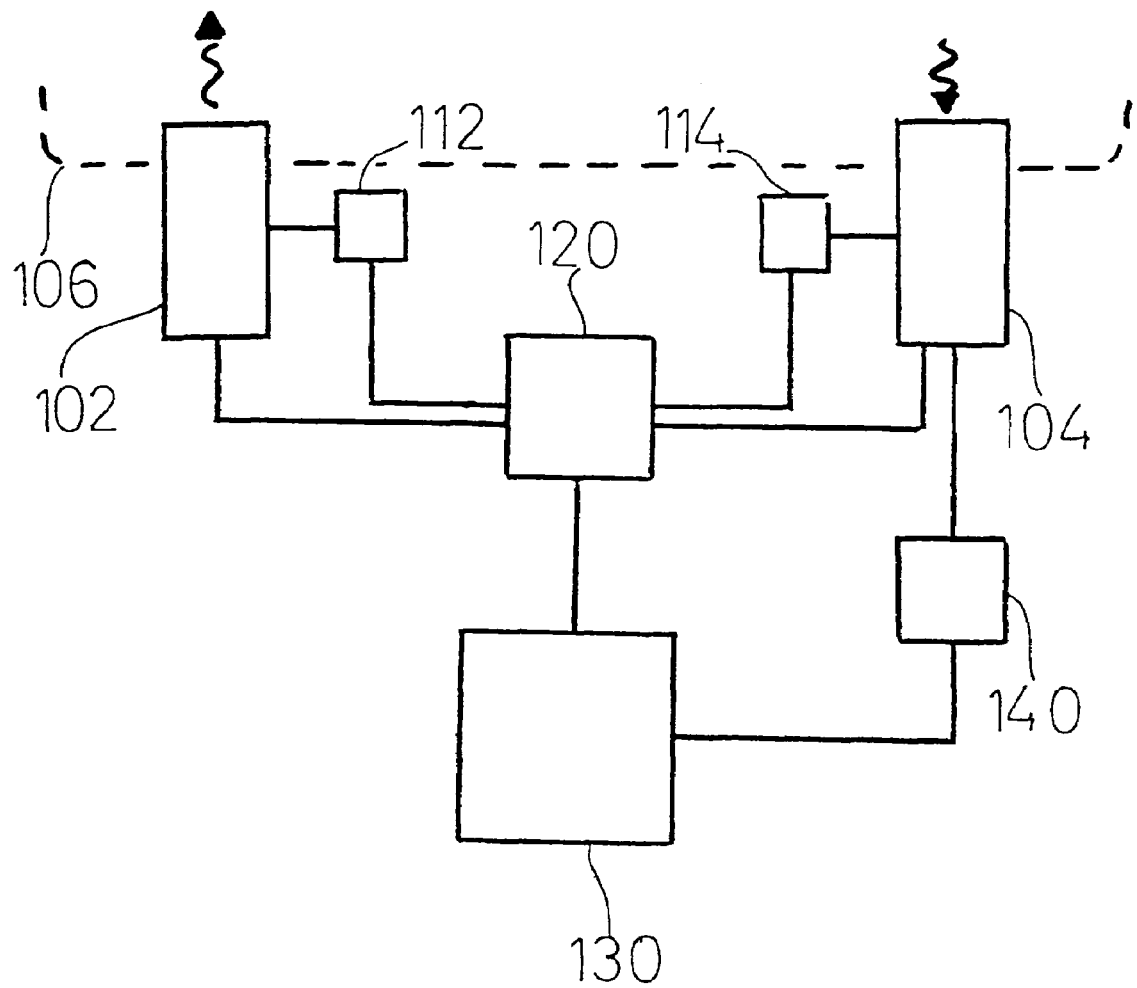
FIG. 6 Schematic representation of a preferred circuit diagram for light introduction means, detector, checking device, output device and further components.

In FIG. 6 there is schematically illustrated a preferred circuit diagram of light introduction means, detector, checking device, output device and further components of an inventive device.

The illustrative device includes a light introduction means 102 and a detector 104 (for conversion or transformation of light signals into detection signals), which respectively are embedded in a shield 106 indicated with dashed lines.

The light introduction means 102 is connected to a first switch element 112, the detector 104 with a second switch element 114. The switch 112 associated with the light introduction means 102 is therein so arranged, that it can be actuated upon contact between the light introduction means 102 and the positionally fixed substrate, when a sufficient force (exceeding a minimum threshold) is exercised upon a light introduction means 102 in the light introducing device; the switch element 114 associated with the detector 104 is in analogous manner so arranged, that upon contact between the detector 104 and a positionally fixed substrate it can be actuated, in that the detector 104 is pressed against the substrate.

Both switch elements 112, 114 are connected with a control unit 120, which for its part controls the operation of the light introduction means 102, the detector 104 and an output device 130, which during measurement operation is supplied with the detection signal from the detector 104 via an evaluation unit 140.

The mentioned components are so connected to each other, that the control unit 120, in the case of a not correct positioning of the light introduction means 102 and detector 104 relative to a substrate, works with the output device 130 such that this produces a malfunction signal and works together with the light introduction means 102 such that this is prevented from operation.

The output device 130 as well as the light introduction means 102 are on the other hand (provided that a suitable source of energy is supplied to the device) automatically activated by the control unit 120, that is, the light introduction means is turned on and the output of the detection signal via the output device 130 is begun when the detector 104 and the light introduction means 102 are simultaneously in prescribed manner brought into contact with the substrate.

The measurement is carried out in such a manner, that (a) the not shown energy supply of the device is switched on and (b) the light introduction means 102 as well as the detector 104 are so placed upon the biological tissue to be examined and pressed there-against, that sufficient force (respectively exceeding a minimal threshold value) are exercised upon the light introduction means 102 and upon the detector 104. Thereby the switch elements 112, 114 are actuated and the control unit 120 is provided with the appropriate contact signals. The control unit 120 then switches the light introduction means 102 and the detector 104 on and places the output device 130 in condition that it can display the detection signals originating from the detector 104 and subsequently further process these via an evaluation unit 140.

The invention claimed is:

1. A device (1) for examination of biological tissue, comprising:
   a light introduction means (102) configured to introduce visible and/or near-infrared light into the biological tissue,
   a detector (104) configured to transform light signals emitted from the biological tissue into detection signals,
   an output device (130) associated with the detector (104) and configured to output information derived from the detection signals,
   a shield (20; 106), the light introduction means (102) and the detector (104) being embedded in the shield,
   a grip part (10) forming a housing configured to receive at least one of an energy source, a display unit, an evaluation unit, and an entry keypad, the grip part (10) being rigidly connected with the shield (20) via a connecting piece,
   a checking device configured to verify appropriate positioning of at least one of the light introduction means (102), the detector, and the shield (20; 106) relative to a substrate, wherein the shield (20; 106) includes an area between the light introduction means (102) and the detector (104), whereby the light introduction means, the detector (104) and therebetween lying areas of the shield (20; 106) are configured to be brought into contact with a surface of the substrate such that the shield (20; 106) during operation of the light introduction means (102) prevents the propagation of light from the light introduction means along the surface of the substrate to the detector (104).

2. The device according to claim 1, wherein the checking device includes one or more assemblies, which are arranged in order to determine whether at least one of the light introduction means (102), the detector, and the shield (20; 106) are in contact with the substrate in a prescribed manner.

3. The device according to claim 1, wherein the checking device includes a control element in connection with the detector (104), which compares the light signals received by the detector (104) with a predetermined threshold value and is so associated with at least one of
   (a) the output device (130), wherein said output device either emits a malfunction or error signal or no information; and
   (b) the light introduction means (102), such that the light introduction means is prevented from becoming operational, when the light signal received from the detector (104) exceeds a predetermined threshold.

4. The device according to claim 1, wherein the checking device includes a measuring device configured to measure the electrical resistance in an area between the light introduction means (102) and detector (104), wherein the checking device is so arranged, that it cooperates with at least one of
   (a) the output device (130) such that the output device either emits a malfunction signal or no information dependent upon the detection signals;
   (b) the light introduction means (102), such that an operation thereof is prevented; and
   (c) the detector (104), such that an operation thereof is prevented when a predetermined resistance threshold value is exceeded.

5. The device according to claim 1, wherein the checking device includes a measuring device configured to measure the electrical capacitance in the immediate environment of the light introduction means (102) or the detector (104) or in an area between the light introduction means (102) and detector (104), wherein the checking device is so arranged, that it the checking device cooperates with at least one of
   (a) the output device (130) such that the output device emits a malfunction signal or no information dependent upon the detection signals;
   (b) the light introduction means (102) such that an operation thereof is prevented; and
   (e) the detector (104), such that an operation thereof is prevented, when a predetermined capacitance threshold value is exceeded or not reached.

6. The device according to claim 1, wherein the shield (20; 106) includes a soft, elastic deformable material adapted for lying against a possibly curved substrate surface.

7. The device according to claim 1, wherein the shield (20; 106) is configured to be so positioned or provided for examination of the brain relative to (a) the brain proximal surface of a head and (b) the detector (104), such that the detector (104) in its detection position is shielded from extraneous light at least in the frequency of the introduced light.

8. The device according to claim 1, wherein the light introduction means (102) and the detector (104) are provided with a spacing of 4-6 cm.

9. A device (1) for examination of biological tissue, comprising:
   a light introduction means (102) configured to introduce visible and/or near-infrared light into the biological tissue,
   a detector (104) configured to transform light signals emitted from the biological tissue into detection signals,
   an output device (130) associated with the detector (104) and configured to output information derived from the detection signals,
   a shield (20; 106), the light introduction means (102) and the detector (104) being embedded in the shield,
   a grip part (10) forming a housing configured to receive at least one of an energy source, a display unit, an evaluation unit, and an entry keypad, the grip part (10) being rigidly connected with the shield (20) via a connecting piece,
   a checking device configured to verify appropriate positioning of at least one of the light introduction means (102), the detector, and the shield (20; 106) relative to a substrate,
   wherein the checking device includes at least one of
      a first switch element (112) associated with the light introduction means (102), wherein the first switch element (112) and the light introduction means (102) are so arranged, that upon contact between the light introduction means and the substrate the first switch element (112) is actuated, in that at least one of the light introduction means (102) and the shield (20; 106) is/are pressed against the substrate; and
      a second switch element (114) for the detector (104), wherein this the second switch element (114) and the detector (104) are so arranged, that upon contact between the detector (104) and a locally fixed substrate the second switch element (114) is actuated, in that at least one of the detector (104) and the shield (20; 106) is/are pressed against the substrate, wherein the checking device includes both the first switch element (112) for the light introduction means (102) as well as the second switch element (114) for the detector (104), wherein the checking device is operably associated with at least one of the output device (130), the light introduction means (102), and the detector (104), in such a manner, that only during simultaneous actuation of the first and second switch elements (112 or as the case may be 114) an output of the detection signals via at least one of the output device (130), an operation of the light introduction means (102), and an operation of the detector (104) is allowed.

10. A device (1) for examination of biological tissue, comprising:
   a light introduction means (102) configured to introduce visible and/or near-infrared light into the biological tissue,
   a detector (104) configured to transform light signals emitted from the biological tissue into detection signals,
   an output device (130) associated with the detector (104) and configured to output information derived from the detection signals,
   a shield (20; 106), the light introduction means (102) and the detector (104) being embedded in the shield,
   a grip part (10) forming a housing configured to receive at least one of an energy source, a display unit, an evaluation unit, and an entry keypad, the grip part (10) being rigidly connected with the shield (20) via a connecting piece,
   a checking device configured to verify appropriate positioning of at least one of the light introduction means (102), the detector, and the shield (20; 106) relative to a substrate, wherein the shield (20; 106) includes an elastic area, in which the detector (104) and the light introduction means (102) are so embedded that they carry out a relative movement relative to each other via the shield (20; 106) lying between them and are conformable to various head shapes and curvatures.

11. The device according to claim 10, wherein a spacer is provided, which maintains essentially constant a spacing between the light introduction means (102) and the detector (104) during variations in a curvature of the shield surface measured along the curvature.

12. A process for determining optical characteristics of biological tissue, the process comprising:
   providing a device (1) for examination of biological tissue, the device comprising:
      a light introduction means (102) configured to introduce visible and/or near-infrared light into the biological tissue,
      a detector (104) configured to transform light signals emitted from the biological tissue into detection signals,
      an output device (130) associated with the detector (104) and configured to output information derived from the detection signals,
      a shield (20; 106), the light introduction means (102) and the detector (104) being embedded in the shield,
      a grip part (10) forming a housing configured to receive at least one of an energy source, a display unit, an evaluation unit, and an entry keypad, the grip part (10) being rigidly connected with the shield (20) via a connecting piece,
      a checking device configured to verify appropriate positioning of at least on of the light introduction means (102), the detector, and the shield (20; 106) relative to a substrate, wherein the shield (20; 106) includes an area between the light introduction means (102) and the detector (104), whereby the light introduction means, the detector (104) and therebetween lying areas of the shield (20; 106) are configured to be brought into contact with a surface of the substrate such that the shield (20; 106) during operation of the light introduction means (102) prevents propagation of light from the light introduction means along the surface of the substrate to the detector (104);
   positioning the light introduction means (102) for introduction of at least one of visible and near-infrared light into the biological tissue at a prescribed position relative to a predetermined light entry location associated with the biological tissue;
   positioning the detector (104) for detecting light exiting from the biological tissue at a prescribed position relative to a predetermined light exit location associated with the biological tissue;
   arranging the shield (20; 106) relative to the biological tissue and the detector (104) so that the detector (104) in a detection position is shielded against extraneous light at least in a visible and/or near-infrared light wavelength region;
   verifying appropriate positioning of at least one of the light introduction means (102), the detector, and the shield (20; 106) relative to a substrate by a checking device; and
   introducing visible or near-infrared light from the light introduction means into the biological tissue and detecting light exiting from the biological tissue by the detector (104).

* * * * *